(12) United States Patent
Imai et al.

(10) Patent No.: US 7,263,158 B2
(45) Date of Patent: Aug. 28, 2007

(54) X-RAY CT APPARATUS

(75) Inventors: Yasuhiro Imai, Tokyo (JP); Akihiko Nishide, Tokyo (JP); Mitsuru Yahata, Tokyo (JP); Masaya Kumazaki, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/431,036

(22) Filed: May 9, 2006

(65) Prior Publication Data

US 2006/0256922 A1 Nov. 16, 2006

(30) Foreign Application Priority Data

May 11, 2005 (JP) ............................. 2005-138025

(51) Int. Cl.
*G01N 23/08* (2006.01)

(52) U.S. Cl. ........................................ 378/19; 378/114

(58) Field of Classification Search ................. 378/19, 378/4, 115–116; 250/370.09
See application file for complete search history.

(56) References Cited

U.S. PATENT DOCUMENTS

| | | | |
|---|---|---|---|
| 5,218,533 A | 6/1993 | Schanen | |
| 5,220,589 A | 6/1993 | Gard | |
| 6,081,576 A | 6/2000 | Schanen et al. | |
| 6,157,696 A * | 12/2000 | Saito et al. | 378/19 |
| 6,359,957 B1 * | 3/2002 | Toth | 378/19 |
| 6,362,478 B1 | 3/2002 | McDaniel et al. | |
| 6,707,876 B2 * | 3/2004 | Tanigawa | 378/19 |

FOREIGN PATENT DOCUMENTS

| | | |
|---|---|---|
| JP | 2001-212128 | 8/2001 |
| JP | 2003-144429 | 5/2003 |

* cited by examiner

*Primary Examiner*—Hoon Song
(74) *Attorney, Agent, or Firm*—Armstrong Teasdale LLP

(57) ABSTRACT

With the object of realizing an X-ray CT apparatus which performs a plurality of pieces of imaging small in resolution degradation too simultaneously while suppressing an expansion of a data acquisition section that receives an electric signal of an X-ray detector, such an array that X-ray detectors in a channel direction are operated with the two as one pair is made by first detector switching means of a switching unit. This array moved by one X-ray detector in the channel direction is alternately repeated in the row or channel direction. Therefore, even when the number of receivers is small, data extending over a wide imaging range can simultaneously be collected while the degradation of resolution is being suppressed to a minor degree. By extension, imaging more coincident with an operator-aimed image can be done by making the switching use of imaging in high resolution.

19 Claims, 12 Drawing Sheets

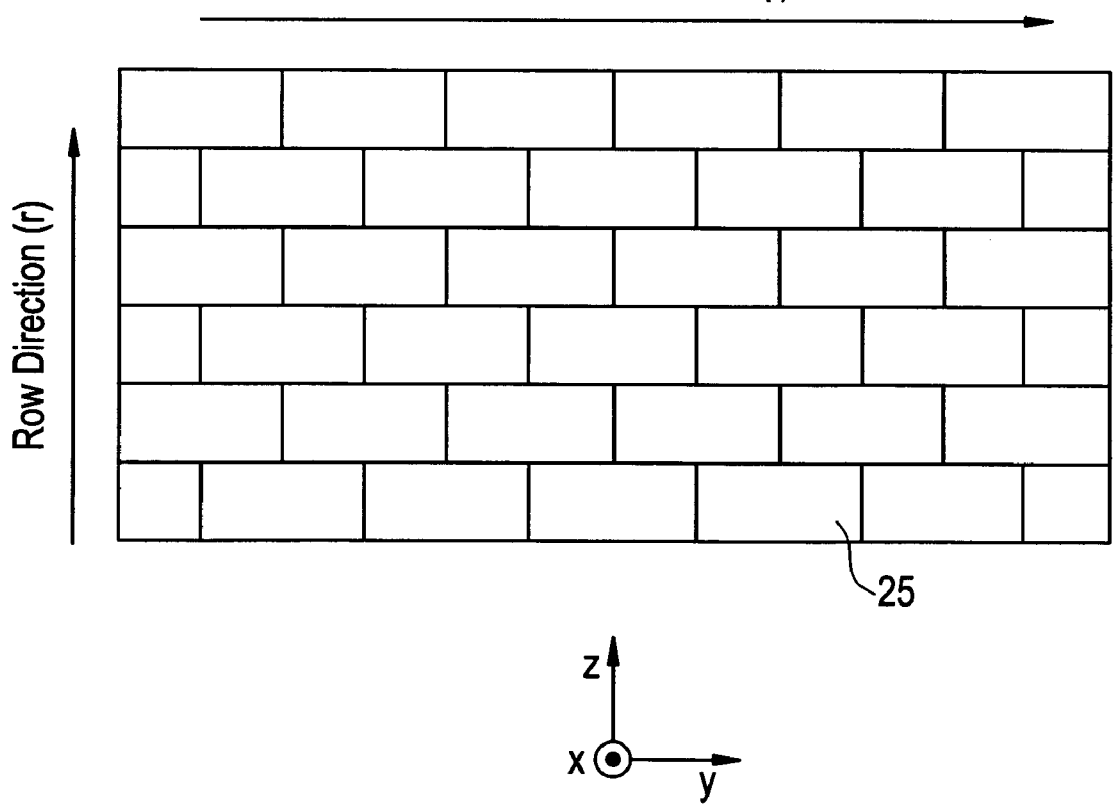

Channel Direction (i)

Channel Direction (i)

Row Direction (r)

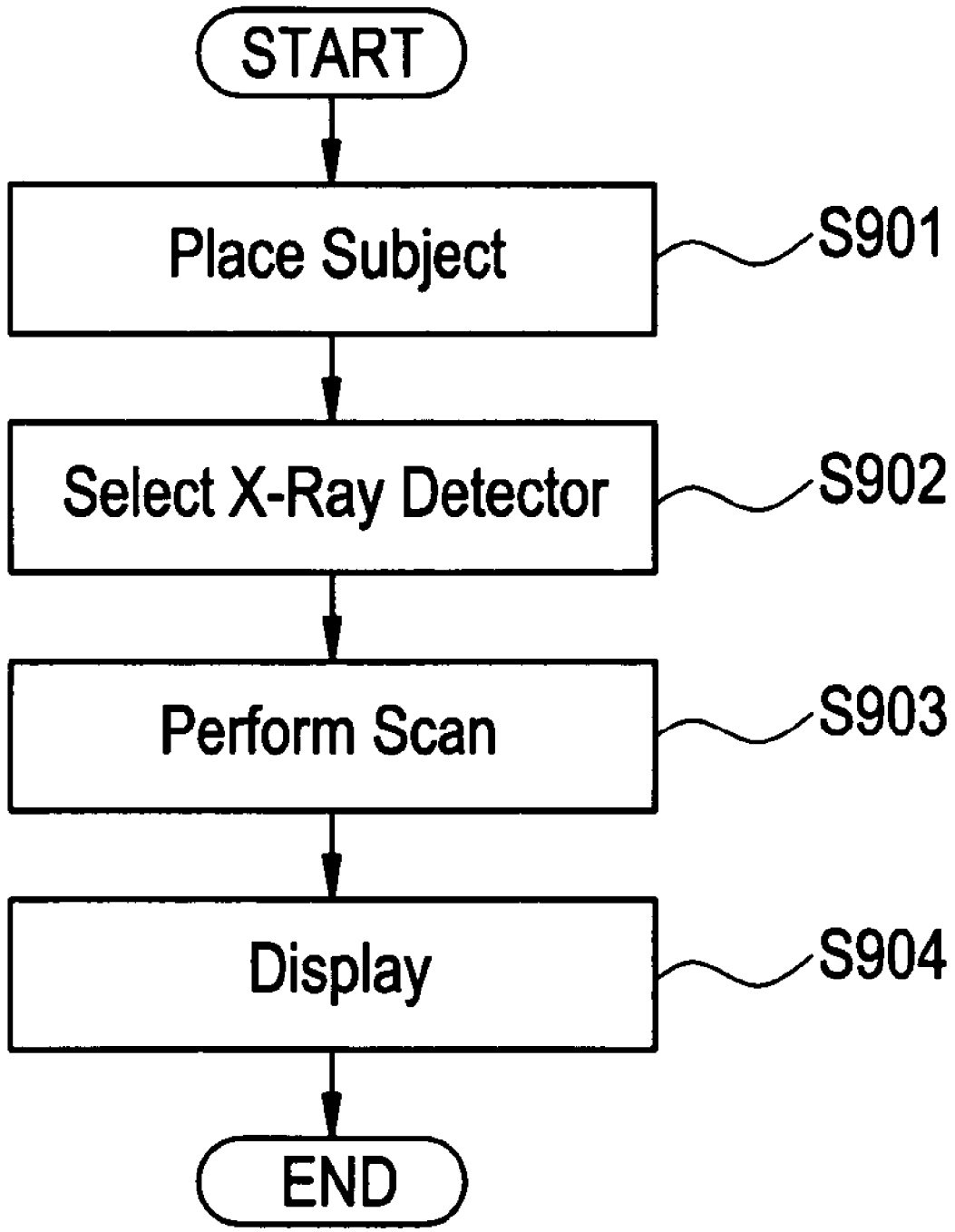

X-RAY CT APPARATUS

CROSS REFERENCE TO RELATED APPLICATIONS

This application claims benefit of Japan Application No. 2005-138025 filed May 11, 2005.

BACKGROUND OF THE INVENTION

The present invention relates to an X-ray CT apparatus which applies a cone X-ray beam spread in fan form with a thickness and detects the X-ray beam by X-ray detectors two-dimensionally arranged in a plane approximately orthogonal to the direction of its application.

Each of X-ray detectors employed in an X-ray CT apparatus has recently been advanced in multichanneling thereof in a scan direction and multirowing thereof in a thickness direction with advances in solid-state X-ray detectors. For instance, each of X-ray detectors in a channel direction results in one having about 1000 channels, whereas each of X-ray detectors in a thickness direction results in one having about several tens of rows (refer to a patent document 1, for example).

Under such circumstances, the X-ray CT apparatus needs a large number of electronic circuit portions at a data acquisition section which amplifies and processes an electric signal detected by the corresponding X-ray detector. The X-ray CT apparatus incorporates these electronic circuit portions in a rotational section lying in a gantry and is rotated together with an X-ray tube and the X-ray detectors to collect or acquire data. Thus, the data acquisition section may preferably be compact. Providing the electronic circuit portions corresponding to all the X-ray detectors in a one-to-one relationship is not easy in terms of the efficiency of accommodation thereof into the rotational section, the cost thereof, etc.

Therefore, a plurality of X-ray detectors, e.g., two channels in a channel direction are electrically connected to each other to function as one channel. They have been connected to the electronic circuit portions of the data acquisition section. Thus, the electronic circuit portions smaller in number than the X-ray detectors are capable of performing imaging using the X-ray CT apparatus.

[Patent Document 1] Japanese Unexamined Patent Publication No. 2003-144429 (Page 6 and FIG. 3)

According to the background art, however, the resolution of an imaged X-ray CT image is degraded and the X-ray detectors existing in large numbers are not effectively utilized. That is, the resolution of the X-ray CT apparatus is degraded as the size of each X-ray detector in the channel and thickness directions increases. Therefore, the resolution is degraded by electrically connecting a plurality of channels and configuring the same as a large X-ray detector equivalently.

Since the small X-ray detectors exist in large numbers, the X-ray CT apparatus is capable of originally performing imaging in high resolution. However, this imaging in the high resolution is restricted by electrically connecting the two channels in the channel direction.

In particular, the multichanneling and multirowing of the X-ray detectors are carried out with relative ease with the advances in the solid-state X-ray detectors. On the other hand, it is not easy to increase the electronic circuit portions of the data acquisition section in terms of the above-described efficiency of accommodation and cost.

It is important from these points to consider how an X-ray CT apparatus that performs a plurality of pieces of imaging small in resolution degradation too simultaneously while suppressing an expansion of the data acquisition section that receives the electric signal of the X-ray detector, would be realized.

SUMMARY OF THE INVENTION

Therefore, an object of the present invention is to provide an X-ray CT apparatus which performs a plurality of pieces of imaging small in resolution degradation too simultaneously while suppressing an expansion of a data acquisition section that receives an electric signal of an X-ray detector.

In order to solve the above problems and attain the above object, an X-ray CT apparatus according to the invention of a first aspect comprises an X-ray tube which applies a cone X-ray beam spread in a thickness direction thereof, an X-ray detector which is two-dimensionally arranged in a plane approximately orthogonal to the direction of application of the X-ray beam and which detects the X-ray beam and converts the same to an electric signal, and a data acquisition section having receivers each amplifying the electric signal, wherein the data acquisition section has a switching unit which turns on and off wirings for electrically connecting the X-ray detector and the receivers and selects the X-ray detector for performing the detection, and wherein the switching unit has composite detector selecting means placed within a plane of the two-dimensionally arranged X-ray detector and in which an electrical connection for allowing the two X-ray detectors adjacent in a coordinate-axis direction indicative of an X-ray detector position in the thickness direction or in a channel direction orthogonal to the thickness direction to operate as one composite detector is repeatedly performed in the coordinate-axis direction, and an electrical connection in which a position of the repetition of the electrical connection is shifted in the coordinate-axis direction by one X-ray detector is performed between the X-ray detectors adjacent in an orthogonal-axis direction normal to the coordinate-axis direction.

In the invention according to the first aspect, the data acquisition section turns on and off wirings for electrically connecting the X-ray detector and the receivers by the switching unit for selecting the corresponding X-ray detector. The switching unit repeatedly performs, through the composite detector selecting means, the electrical connection for allowing the two X-ray detectors to operate as one composite detector, in the coordinate-axis direction indicative of the X-ray detector position in the thickness direction of the two-dimensionally arranged X-ray detector or in the channel direction orthogonal to the thickness direction and performs the electrical connection in which the position of the repetition of the electrical connection is shifted in the coordinate-axis direction by one X-ray detector, between the X-ray detectors adjacent in the orthogonal-axis direction normal to the coordinate-axis direction.

An X-ray CT apparatus according to the invention of a second aspect is provided wherein in the invention described in the first aspect, the composite detector selecting means includes first detector selecting means in which the coordinate-axis direction is defined as the channel direction.

An X-ray CT apparatus according to the invention of a third aspect is provided wherein in the invention described in the first or second aspect, the composite detector selecting means has second detector selecting means in which the coordinate-axis direction is defined as a row direction corresponding to the direction in which the thickness of the X-ray beam exists.

In the invention of the third aspect, the composite detector selecting means defines the coordinate-axis direction as the row direction by means of the second detector selecting means.

An X-ray CT apparatus according to the invention of a fourth aspect is provided wherein in the invention described in any one of the first through third aspects, the switching unit has third detector selecting means which electrically connects one of the receivers and one of the X-ray detectors.

In the invention of the fourth aspect, the switching means or unit electrically connects the receivers and the X-ray detector in a one-to-one relationship by means of the third detector selecting means.

An X-ray CT apparatus according to the invention of a fifth aspect is provided wherein in the invention described in the second, third and fourth aspects, the data acquisition section includes switching means which allows the first through third detector selecting means to operate by switching.

An X-ray CT apparatus according to the invention of a sixth aspect is provided wherein in the invention described in the fifth aspect, the switching means performs switching to the third detector selecting means when a conventional scan or a cine scan is done.

An X-ray CT apparatus according to the invention of a seventh aspect is provided wherein in the invention described in the fifth or sixth aspect, the switching means performs switching to the first or second detector selecting means when simultaneous collection of data, which is performed by the conventional scan or the cine scan, is carried out in a wider imaging range.

An X-ray CT apparatus according to the invention of an eighth aspect is provided wherein in the invention described in any one of the fifth through seventh aspects, the switching means performs switching to the third detector selecting means when a helical scan is done.

An X-ray CT apparatus according to the invention of a ninth aspect is provided wherein in the invention described in any one of the fifth through eighth aspects, the switching means performs switching to the first or second detector selecting means when simultaneous collection of data, which is performed by the helical scan, is carried out in a wider imaging range.

An X-ray CT apparatus according to the invention of a tenth aspect is provided wherein in the invention described in any one of the first through ninth aspects, the X-ray detector includes scintillators.

In the invention of the tenth aspect, the X-ray detector converts X rays to light.

An X-ray CT apparatus according to the invention of an eleventh aspect is provided wherein in the invention described in any one of the first through tenth aspects, the data acquisition section is accommodated in a rotational section including the X-ray tube and the X-ray detector.

An X-ray CT apparatus according to the invention of a twelfth aspect is provided wherein in the invention described in any one of the first through eleventh aspects, the switching unit includes FETs each of which performs the turning on/off.

In the invention of the twelfth aspect, the switching unit performs on/off at high speed by means of FETs.

An X-ray CT apparatus according to the invention of a thirteenth aspect is provided wherein in the invention described in any one of the first through twelfth aspects, the data acquisition section includes the receivers smaller than the X-ray detectors in number.

In the invention of the thirteenth aspect, the data acquisition section sets the number of the receivers smaller than the number of the X-ray detectors.

An X-ray CT apparatus according to the invention of the fourteenth aspect is provided wherein in the invention described in the fourth and thirteenth aspects, the third detector selecting means reduces the number of X-ray detectors selected in either the coordinate-axis direction or the orthogonal-axis direction.

In the invention of the fourteenth aspect, the third detector selecting means sets either the orthogonal-axis direction or the coordinate-axis direction to high resolution.

An X-ray CT apparatus according to the invention of a fifteenth aspect is provided wherein in the invention described in any one of the first through the fourteenth aspects, the X-ray detectors set the positions of the respective X-ray detectors arranged in the coordinate-axis direction as the same positions as viewed in the orthogonal-axis direction.

In the invention of the fifteenth aspect, the positions of the X-ray detectors are placed in perfect matrix form.

An X-ray CT apparatus according to the invention described in any one of the first through fourteenth aspects is provided wherein the X-ray detectors alternately perform an array of the X-ray detectors disposed at equal intervals in the coordinate-axis direction and a movement array in which the array thereof is shifted by half of each equal interval in the coordinate-axis direction, with respect to the alternate X-ray detectors in the orthogonal-axis direction.

In the invention of the sixteenth aspect, the movement array of the X-ray detectors each shifted by half of each equal interval in the coordinate-axis direction is alternately performed repeatedly in the orthogonal-axis direction.

An X-ray CT apparatus according to the invention of a seventeenth aspect is provided wherein in the invention described in the sixteenth aspect, the X-ray detectors include X-ray detectors whose each length in the coordinate-axis direction is equal to half of the X-ray detector, which are disposed at ends in the coordinate-axis direction, of the movement array.

In the invention of the seventeenth aspect, the X-ray detectors prevent the occurrence of their depressions and projections at the ends of the movement array in the coordinate-axis direction.

An X-ray CT apparatus according to the invention of an eighteenth aspect is provided wherein in the invention described in any one of the first through fourteenth aspects, the X-ray detectors are configured in such a manner that an array of the X-ray detectors disposed at equal intervals in the orthogonal-axis direction and a movement array in which the array thereof is shifted by half of each equal interval in the orthogonal-axis direction, are carried out between the X-ray detectors adjacent in the coordinate-axis direction.

In the invention of the eighteenth aspect, the movement array of the X-ray detectors each shifted by half of each equal interval in the orthogonal-axis direction is alternately performed repeatedly in the coordinate-axis direction.

An X-ray CT apparatus according to the invention of a nineteenth aspect is provided wherein in the invention described in the eighteenth aspect, the X-ray detectors include X-ray detectors whose each length in the orthogonal-axis direction is equal to half of the X-ray detector, which are disposed at ends in the orthogonal-axis direction, of the movement array.

In the invention of the nineteenth aspect, the X-ray detectors prevent the occurrence of their depressions and projections at the ends of the movement array in the orthogonal-axis direction.

According to the present invention, as described above, a data acquisition section turns on and off wirings for electrically connecting an X-ray detector and receivers by a switching unit for selecting the corresponding X-ray detector. The switching unit repeatedly performs, through composite detector selecting means, an electrical connection for allowing two X-ray detectors to operate as one composite detector, in a coordinate-axis direction indicative of an X-ray detector position in a thickness direction of the two-dimensionally arranged X-ray detector or in a channel direction orthogonal to the thickness direction and performs an electrical connection in which the position of the repetition of the electrical connection is shifted in the coordinate-axis direction by one X-ray detector, between the X-ray detectors adjacent in an orthogonal-axis direction normal to the coordinate-axis direction. Therefore, the simultaneous collection of data can be performed by the receivers smaller in number than the X-ray detectors and in a wide imaging range in which the degradation of resolution is suppressed to a minor degree. By extension, a low-cost X-ray CT apparatus reduced in the number of receivers is capable of performing various imaging that meet operator's various demands.

Further objects and advantages of the present invention will be apparent from the following description of the preferred embodiments of the invention as illustrated in the accompanying drawings.

BRIEF DESCRIPTION OF THE DRAWINGS

FIG. 5 is an explanatory diagram showing the selection of the X-ray detector by the first detector selecting means.

FIG. 10 is a flowchart showing the operation of the X-ray CT apparatus of the embodiment.

DETAILED DESCRIPTION OF THE INVENTION

A best mode for carrying out an X-ray CT apparatus according to the present invention will be explained below with reference to the accompanying drawings. Incidentally, the present invention is not limited by or to it.

Figure 1:
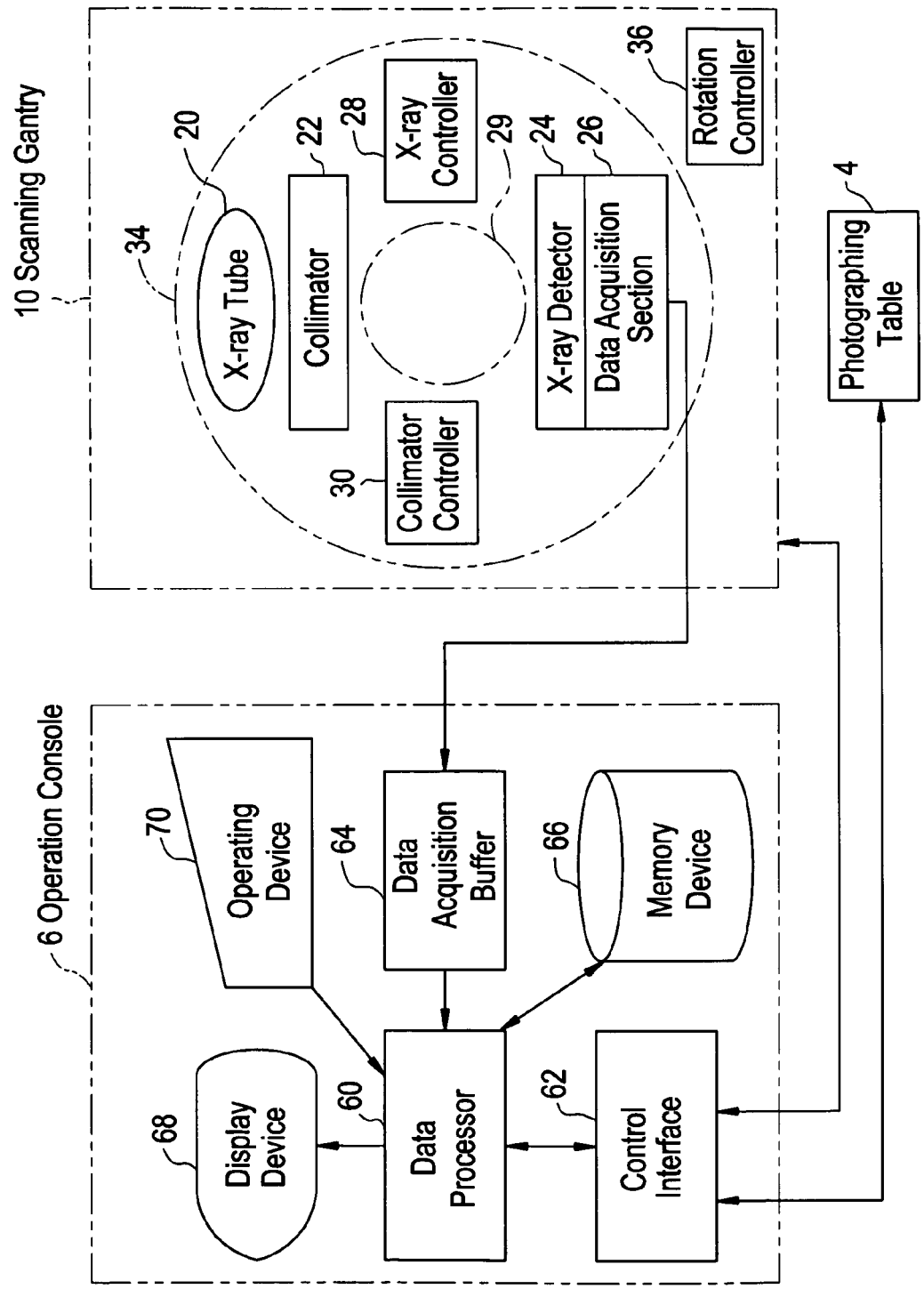
FIG. 1 is a block diagram showing an overall construction of an X-ray CT apparatus.

An overall construction of the X-ray CT apparatus according to the present embodiment will first be explained. FIG. 1 shows a block diagram of the X-ray CT apparatus. As shown in FIG. 1, the present apparatus has a scanning gantry 10 and an operation console 6.

The scanning gantry 10 has an X-ray tube 20. Unillustrated X rays radiated from the X-ray tube 20 are spread in fan form with a thickness and shaped so as to reach a cone X-ray beam, for example, by a collimator 22 and then applied to an X-ray detector 24.

The X-ray detector 24 includes a plurality of scintillators arranged in matrix form in the direction in which the cone X-ray beam spreads. The X-ray detector 24 is configured as a wide multichannel detector in which the plurality of scintillators are arranged in matrix form.

The X-ray detector 24 forms an X-ray incident plane bended in a concave fashion. The X-ray detector 24 is equivalent to, for example, one in which scintillators comprised of inorganic crystals and photo diodes corresponding to optoelectronic transducers, etc. are combined together.

A data acquisition section 26 is connected to the X-ray detector 24. The data acquisition section 26 collects information detected by the individual scintillators of the X-ray detector 24. The application of the X-rays from the X-ray tube 20 is controlled by an X-ray controller 28. Incidentally, the relationship of connection between the X-ray tube 20 and an X-ray controller 28 and the relationship of connection between the collimator 22 and a collimator controller 30 are not shown in the drawing. The collimator 22 is controlled by the collimator controller 30.

The above ones provided between the X-ray tube 20 and the collimator controller 30 are mounted onto a rotational section 34 of the scanning gantry 10. Here, a subject or a body to be examined or a phantom is placed on a photographing table 4 lying within a bore 29 positioned in the center of the rotational section 34. The rotational section 34 is rotated while being controlled by a rotation controller 36 to irradiate X rays from the X-ray tube 20. The X-ray detector 24 detects the penetrated X rays of the subject and phantom as projection information set every views corresponding to rotational angles. Incidentally, the relationship of connection between the rotational section 34 and the rotation controller 36 is not shown in the figure.

The operation console 6 has a data processor 60. The data processor 60 comprises a computer or the like, for example. A control interface 62 is connected to the data processor 60. The control interface 62 is connected to the scanning gantry 10. The data processor 60 controls the scanning gantry 10 through the control interface 62.

The data acquisition section 26, X-ray controller 28, collimator controller 30 and rotation controller 36 provided within the scanning gantry 10 are controlled through the control interface 62. Incidentally, the individual connections of these respective parts and the control interface 62 are not shown in the drawing.

A data acquisition buffer 64 is connected to the data processor 60. The data acquisition buffer 64 is connected to the data acquisition section 26 of the scanning gantry 10.

Data acquired or collected by the data acquisition section 26 are inputted to the data processor 60 through the data acquisition buffer 64.

The data processor 60 performs image reconstruction using the penetrated X-ray signals, i.e., projection information acquired through the data acquisition buffer 64. Also a memory device 66 is connected to the data processor 60. The memory device 66 stores therein the projection information collected into the data acquisition buffer 64, reconstructed tomographic image information and programs for realizing the function of the present apparatus, etc.

A display device 68 and an operating device 70 are respectively connected to the data processor 60. The display device 68 displays the tomographic image information and other information outputted from the data processor 60. The operating device 70 is operated by an operator to input various instructions and information or the like to the data processor 60. The operator interactively operates the present apparatus by using the display device 68 and the operating device 70. Incidentally, the scanning gantry 10, the photographing table 4 and the operation console 6 photograph the subject or phantom to acquire a tomographic image.

Figure 2:
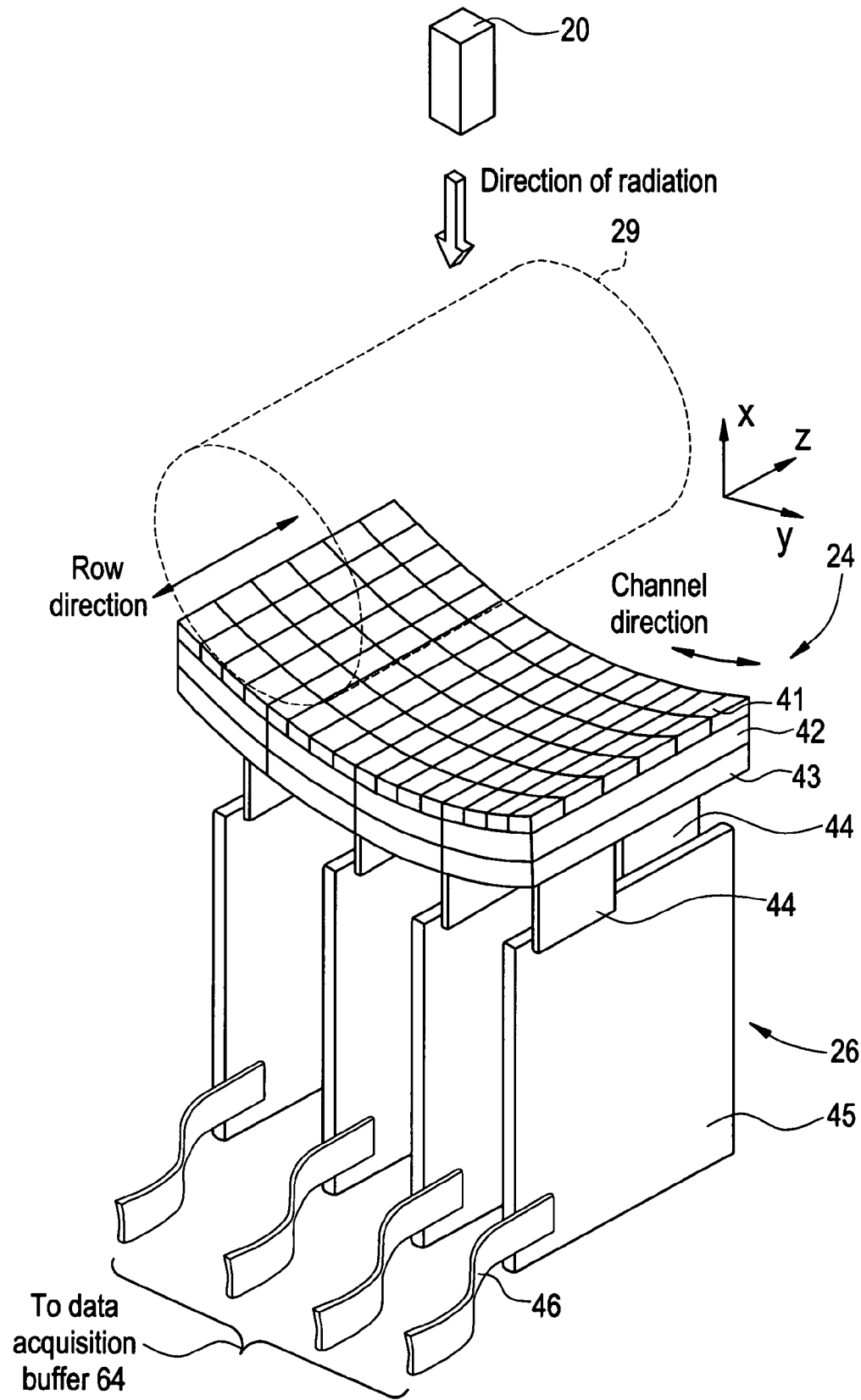
FIG. 2 is an external view illustrating an X-ray tube, an X-ray detector and a data acquisition section of an embodiment.

FIG. 2 shows a three-dimensional layout of the X-ray detector 24 and the data acquisition section 26. The X-ray detector 24 includes scintillators 41 each of which detects a cone X-ray beam generated by the X-ray tube 20, photo diodes 42 each corresponding to an optoelectronic transducer which detects light emitted from the scintillator 41, and a substrate 43.

The scintillators 41 are two-dimensionally arranged in a plane opposite to the cone X-ray beam. When the X rays enter, the scintillators 41 emit light. Now, the scintillators 41 equivalent to the number of approximately 64 rows and about 1000 channels are arranged in a row direction corresponding to the direction of thickness of the cone X-ray beam and a channel direction corresponding to the direction in which the X-ray beam spreads in fan form.

Each of the photo diodes 42 is formed on the substrate 43 and detects the light emitted from the scintillator 41. Here, the photo diodes 42 corresponding to the plural channels are formed on the substrate 43 so as to take an integral structure. In the example illustrated in FIG. 2, the photo diodes 42 corresponding to four channels form an integral structure.

The data acquisition section 26 includes flexible print boards 44, print boards 45 and electric cables 46. Each of the flexible print boards 44 transmits an X-ray-based electric signal detected by the photo diode 42 to its corresponding print board 45. The corresponding print board 45 amplifies the detected X-ray-based electric signal, converts this analog signal to a digital signal and transfers the digital signal to the subsequent-stage data acquisition buffer 64.

Each of the electric cables 46 electrically connect each print board 45 and the data acquisition buffer 64.

Figure 3:
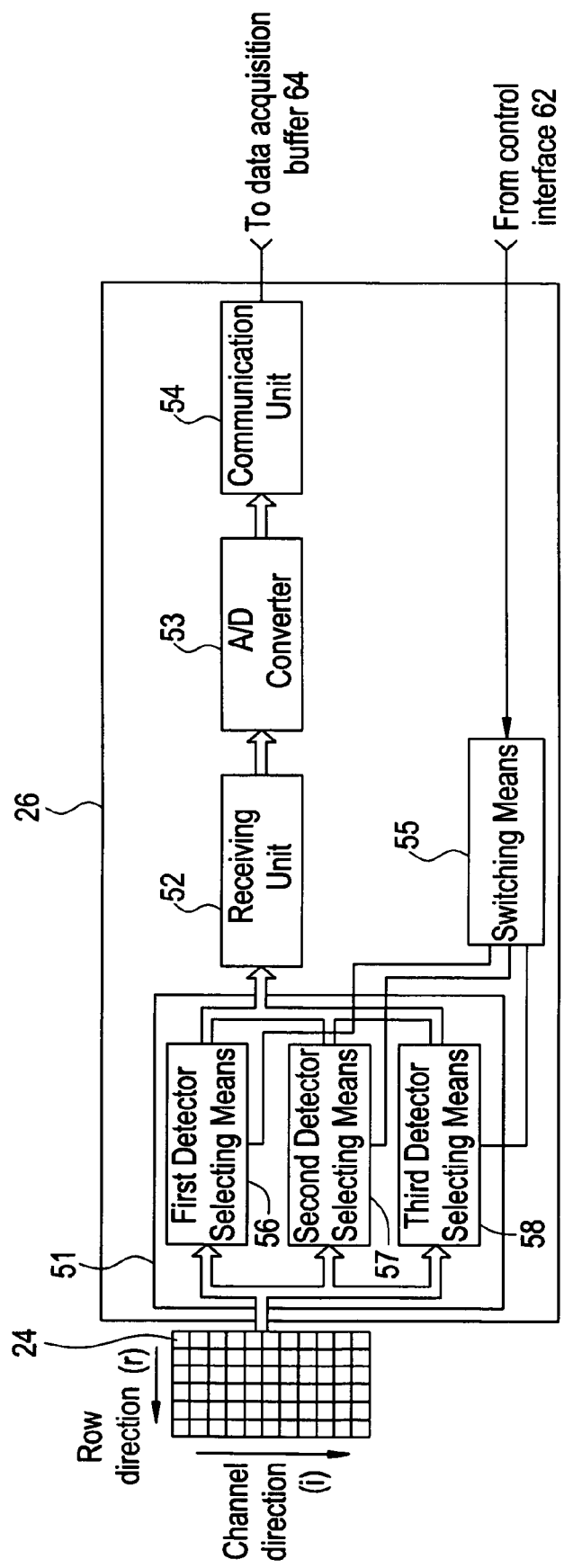
FIG. 3 is a block diagram showing the data acquisition section of the embodiment.

FIG. 3 is a block diagram showing the construction of the data acquisition section 26. The data acquisition section 26 includes a switching unit 51, a receiving unit 52, an A/D converter 53, a communication unit 54 and switching means 55. Incidentally, electric parts constituting these respective portions are disposed on each print board 45 shown in FIG. 2.

The switching unit 51 electrically connects the X-ray detector 24 and the receiving unit 52. Upon such an electrical connection, a switch array in which, for example, FETs (Field Effect Transistors) or the like are arranged in large numbers is used. The switching unit 51 is brought to a fast switchable compact configuration. Further, the switching unit 51 includes first detector selecting means 56, second detector selecting means 57 and third detector selecting means 58 that constitute composite detector selecting means. Incidentally, their configurations will be described in detail later.

The receiving unit 52 comprises a plurality of receivers each of which amplifies an electric signal outputted from the corresponding photo diode 42. Here, the X-ray detector 24 comprises the scintillators 41 and photo diodes 42 which are about equal to approximately 1000×64 in number, whereas the receivers of the receiving unit 52 are set to, for example, about one half the number of the scintillators 41. Thus, data sizes collected into the data acquisition buffer 64 are limited by the number of the receivers.

The A/D converter 53 converts an analog signal received by each of the receivers to a digital signal. The communication unit 54 converts the digital signal from a parallel signal to a serial signal, for example and transfers the same to the data acquisition buffer 64 at high speed.

The switching means 55 performs switching among the first detector selecting means 56, the second detector selecting means 57 and the third detector selecting means 58 of the switching unit 51 in accordance with instructions issued from the control interface 62.

The configurations of the first detector selecting means 56, the second detector selecting means 57 and the third detector selecting means 58 will be explained subsequently. Incidentally, the X-ray detector 24 is assumed to be one configured in the form of a matrix with 12 channels as viewed in the channel direction and 6 rows as viewed in the row direction such as shown in FIG. 3 for simplification of explanation. And a parameter for designating each X-ray detector position in the channel direction is defined as i and a parameter for designating a row position of each X-ray detector in the row direction is defined as r.

Figure 4A:
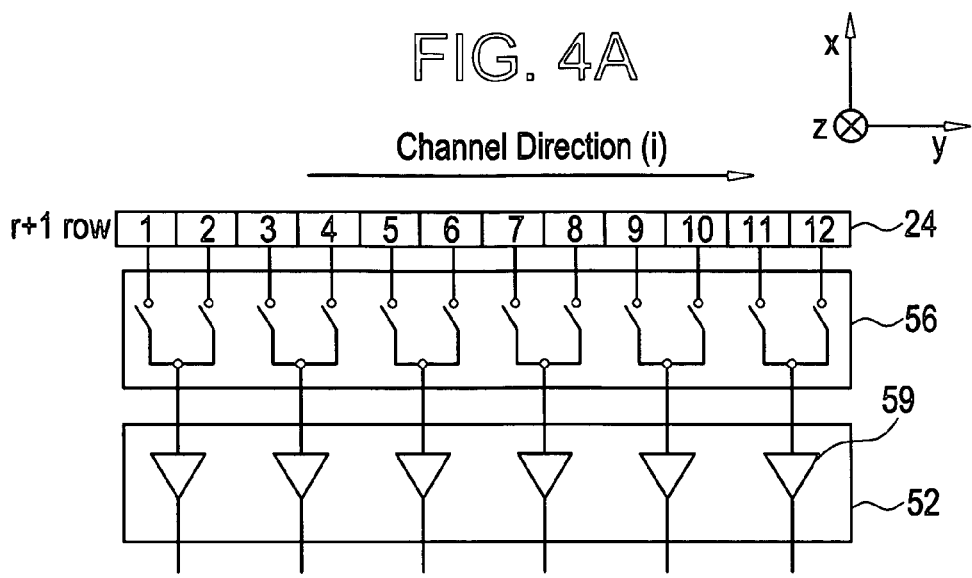
FIGS. 4a, 4b, and 4c are block diagrams illustrating first detector selecting means of the embodiment.
Figure 4B:
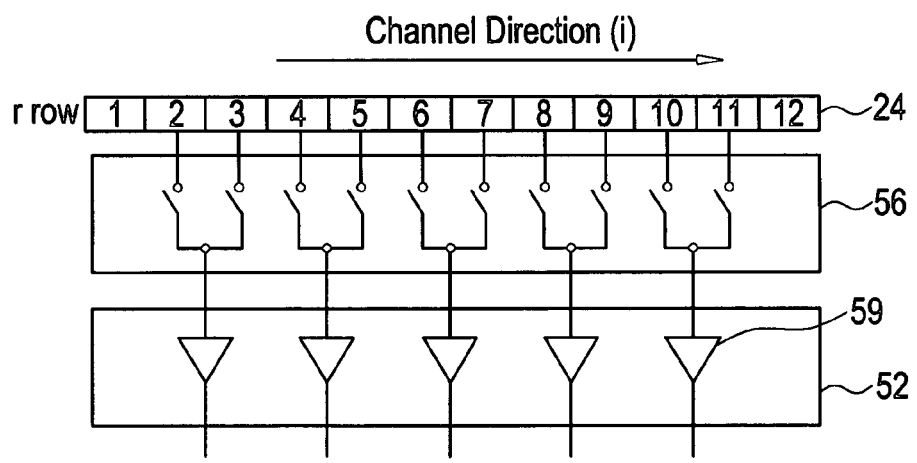
Figure 4C:
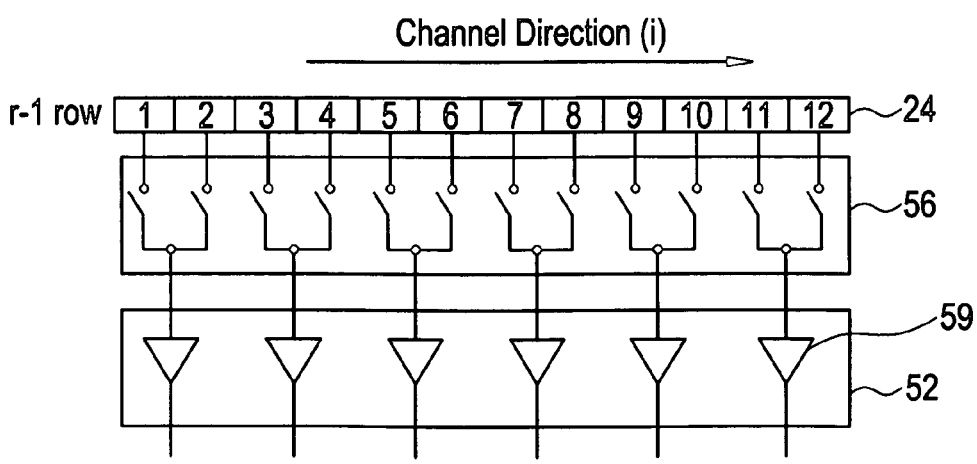

FIG. 4 is a diagram showing the configuration of the first detector selecting means 56 that constitutes the composite detector selecting means. FIGS. 4(A), 4(B) and 4(C) respectively show the X-ray detectors 24, the first detector selecting means 56 and the receiving unit 52 viewed in the channel directions of r+1, r and r−1 rows. Here, row-direction positions r are arbitrary row numbers. In the first detector selecting means 56, a coordinate-axis direction for designating the position of each two-dimensionally-arranged X-ray detector is defined as the channel direction, and an orthogonal-axis direction orthogonal to the coordinate-axis direction is defined as the row direction.

The first detector selecting means 56 comprises switches of the same number as the X-ray detectors 24 and electric wirings for connecting these switches. When the switches are on, the first detector selecting means 56 electrically connects respective adjacent two channels, i.e., channels of channel numbers 1 and 2, 3 and 4, 5 and 6, . . . , 11 and 12 and serves as plural composite detectors with the two as one pair, with respect to the X-ray detector 24 of the r+1 row shown in FIG. 4(A). These electrically-connected terminal outputs are used as the inputs of the respective receivers 59 of the receiving unit 52.

When the switches are on, the first detector selecting means 56 electrically connects respective adjacent two channels moved in the channel direction by one channel as compared with the r+1 row, i.e., channels of channel numbers 2 and 3, 4 and 5, 6 and 7, . . . 10 and 11 and serves as plural composite detectors with the two as one pair, with respect to the X-ray detector 24 of the r row shown in FIG. 4(B). These electrically-connected terminal outputs are used as the inputs of the respective receivers 59 of the receiving unit 52.

When the switches are on, the first detector selecting means 56 electrically connects respective adjacent two channels similar to FIG. 4(A), i.e., channels of channel numbers 1 and 2, 3 and 4, 5 and 6, . . . 11 and 12 and serves as plural composite detectors with the two as one pair, with respect to the X-ray detector 24 of the r−1 row shown in FIG. 4(C). These electrically-connected terminal outputs are used as the inputs of the respective receivers 59 of the receiving unit 52. Similarly to the above subsequently, the electrical connections of electrically-connected arrangements in the channel direction are shifted by one X-ray detector position each time the rows in the row direction are moved.

The switches of the first detector selecting means 56 are all turned on and off in sync with one another by a control signal outputted from unillustrated switching means 55.

FIG. 5 is a diagram showing a two-dimensional arrangement in the channel and row directions, of the composite detectors 25 formed by the first detector selecting means 56 constituting the composite detector selecting means. The composite detector 25 has a structure in which two X-ray detectors 24 are combined in the channel direction. Each time the rows in the row direction differ, the repeated pitch of each composite detector 25 in the channel direction is moved by half in the channel direction.

Figure 6A:
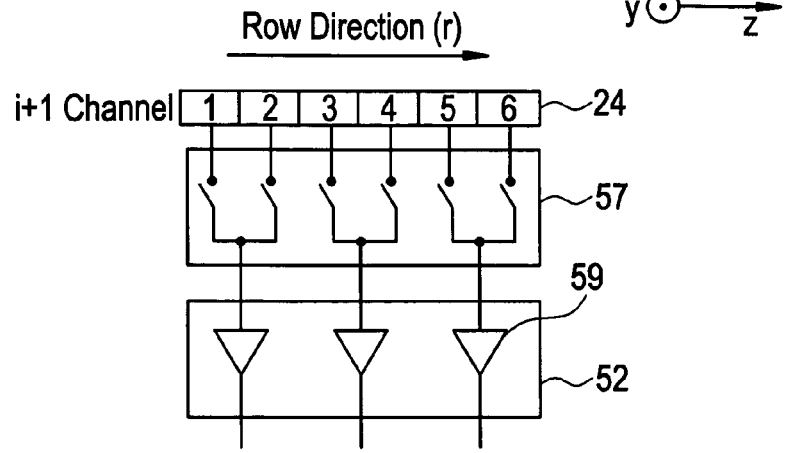
FIGS. 6a, 6b, and 6c are block diagrams illustrating second detector selecting means of the embodiment.
Figure 6B:
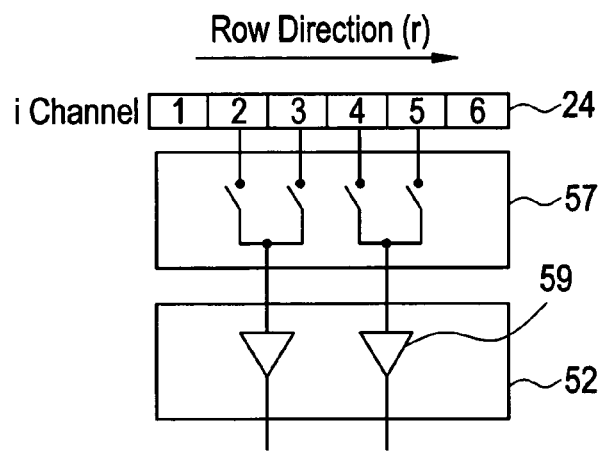
Figure 6C:
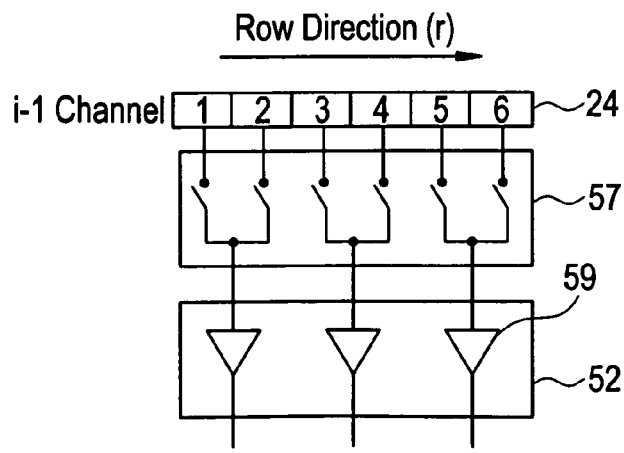

FIG. 6 is a diagram showing the configuration of the second detector selecting means 57 constituting the composite detector selecting means. FIGS. 6(A), 6(B) and 6(C) respectively show the X-ray detectors 24, the second detector selecting means 57 and the receiving units 52 viewed in the row directions of i+1, i and i−1 channels. Here, channel-direction positions i are arbitrary channel numbers. In the second detector selecting means 57, a coordinate-axis direction for designating the position of each two-dimensionally-arranged X-ray detector is defined as the row direction, and an orthogonal-axis direction orthogonal to the coordinate-axis direction is defined as the channel direction.

The second detector selecting means 57 comprises switches of the same number as the X-ray detectors 24 and electric wirings for connecting these switches. When the switches are on, the second detector selecting means 57 electrically connects respective adjacent two rows, i.e., rows of row numbers 1 and 2, 3 and 4, and 5 and 6 and serves as plural composite detectors with the two as one pair, with respect to the X-ray detector 24 of the i+1 channel shown in FIG. 6(A). These electrically-connected terminal outputs are inputted to the respective receivers 59 of the receiving unit 52.

When the switches are on, the second detector selecting means 57 electrically connects respective adjacent two rows moved in the row direction by one row as compared with the i+1 channel, i.e., rows of row numbers 2 and 3, and 4 and 5 and serves as plural composite detectors with the two as one pair, with respect to the X-ray detector 24 of the i channel shown in FIG. 6(B). These electrically-connected terminal outputs are inputted to their corresponding receivers 59 of the receiving unit 52.

When the switches are on, the second detector selecting means 57 electrically connects respective two rows adjacent similarly to FIG. 6(A), i.e., rows of row numbers 1 and 2, 3 and 4, and 5 and 6 and serves as plural composite detectors with the two as one pair, with respect to the X-ray detector 24 of the i−1 channel shown in FIG. 6(C). These electrically-connected terminal outputs are inputted to the respective receivers 59 of the receiving unit 52. Each time the channel is moved, the position of each of the electrically-connected X-ray detectors in the row direction is moved by one to thereby define the second detector selecting means as the composite detector.

Figure 7:
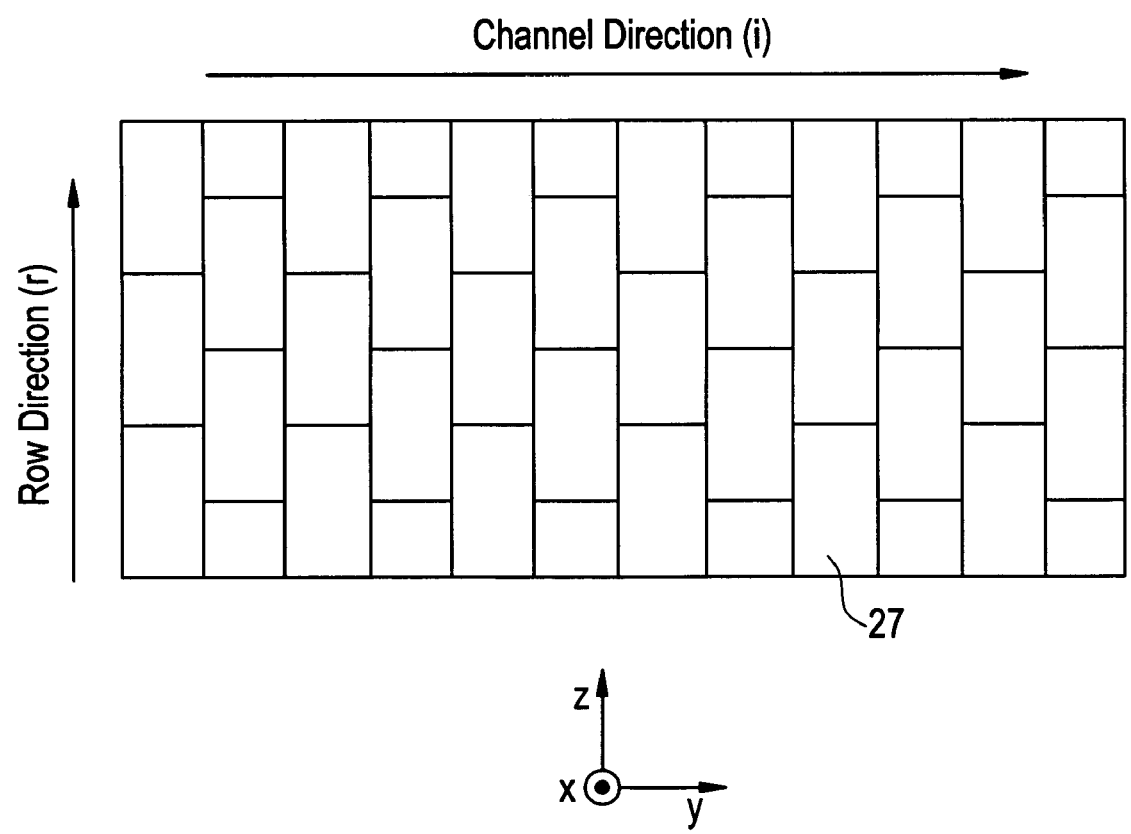
FIG. 7 is an explanatory diagram showing the selection of an X-ray detector by the second detector selecting means.

FIG. 7 is a diagram showing a two-dimensional arrangement in the channel and row directions, of composite detectors 27 formed by second detector selecting means 57 constituting composite detector selecting means. The composite detector 27 has a structure in which two X-ray detectors 24 adjacent in the row direction are combined. Each time the channels differ, the repeated pitch of each composite detector 27 in the row direction is moved by half in the row direction.

Switches of the detector selecting means 57 are all turned on and off in sync with one another by a control signal outputted from unillustrated switching means 55.

Figure 8A:
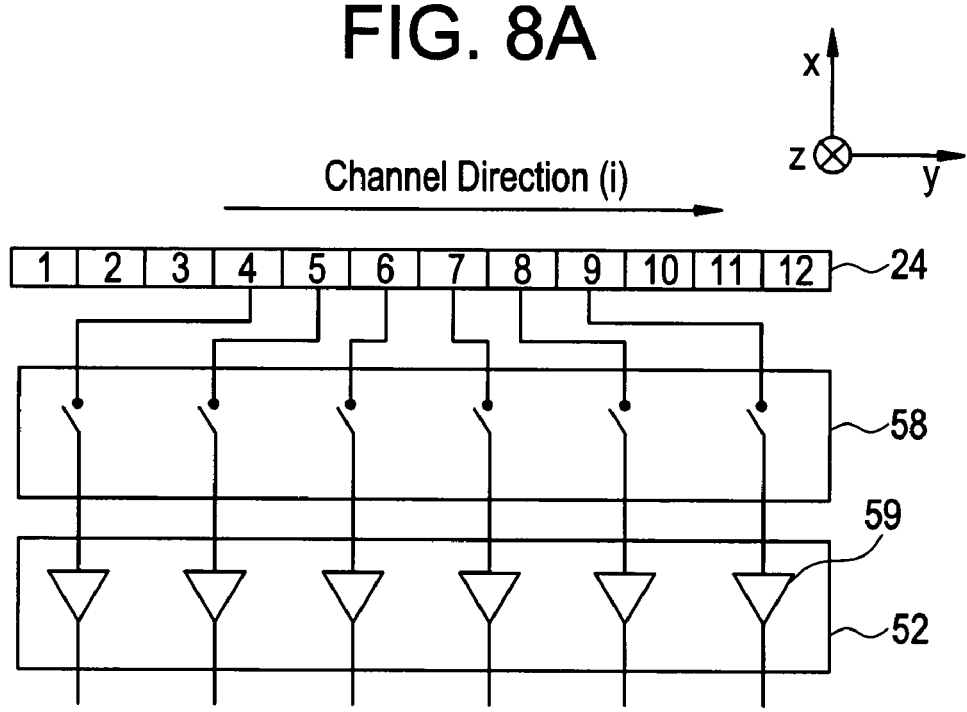
FIG. 8a is a block diagram and FIG. 8b is an explanatory diagram both illustrating third detector selecting means of the embodiment (part 1).

FIG. 8 is a diagram showing the configuration of third detector selecting means 58. FIG. 8(A) illustrates an X-ray detector 24, third detector selecting means 58 and a receiving unit 52 as viewed in the channel direction. Here, a row-direction position r is an arbitrary row number and there is no difference in the present configuration due to the row. When each switch of the third detector selecting means 58 is turned on, the third detector selecting means 58 defines or sets one channel as the input of each receiver 59 of the receiving unit 52. In the example shown in FIG. 8(A), the X-ray detector 24 having channel numbers 4, 5, 6, 7, 8 and 9 corresponds to the inputs of the respective receivers 59 of the receiving unit 52.

Figure 8B:
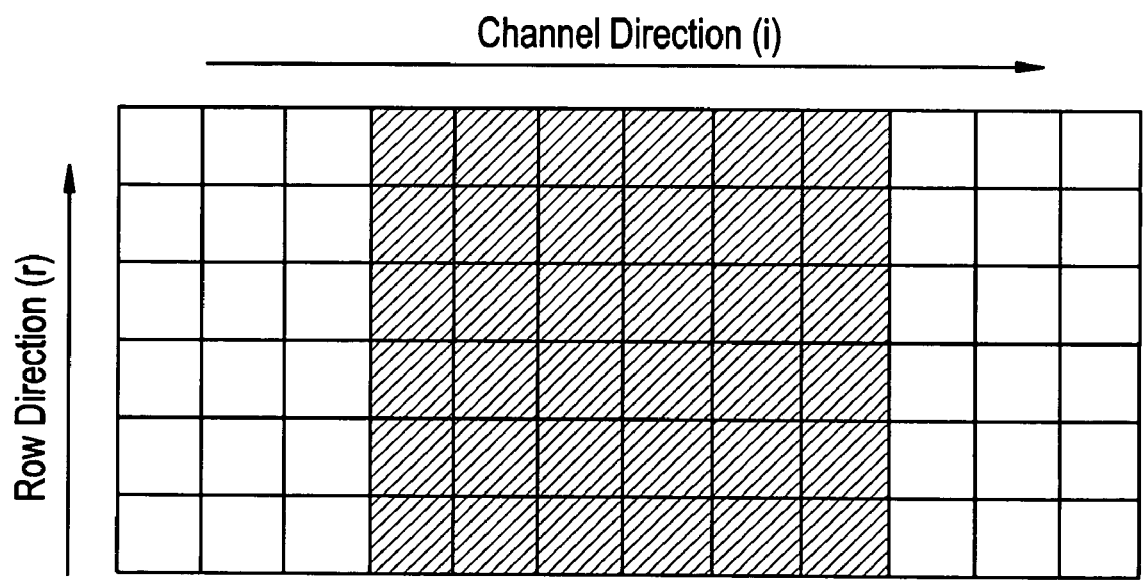

FIG. 8(B) is a diagram showing a two-dimensional arrangement in channel and row directions, of X-ray detectors 24 selected by the third detector selecting means 58. The X-ray detectors 24 in a diagonally shaded area of FIG. 8(B) perform reception and acquire projection information.

Incidentally, the third detector selecting means 58 may be configured such that the X-ray detector 24 and each amplifier of the receiving unit 52 are placed in a one-to-one correspondence. The third detector selecting means 58 may take such a connection that, for example, the number of rows in the row direction decreases and the number of channels in the channel direction increases.

Figure 9A:
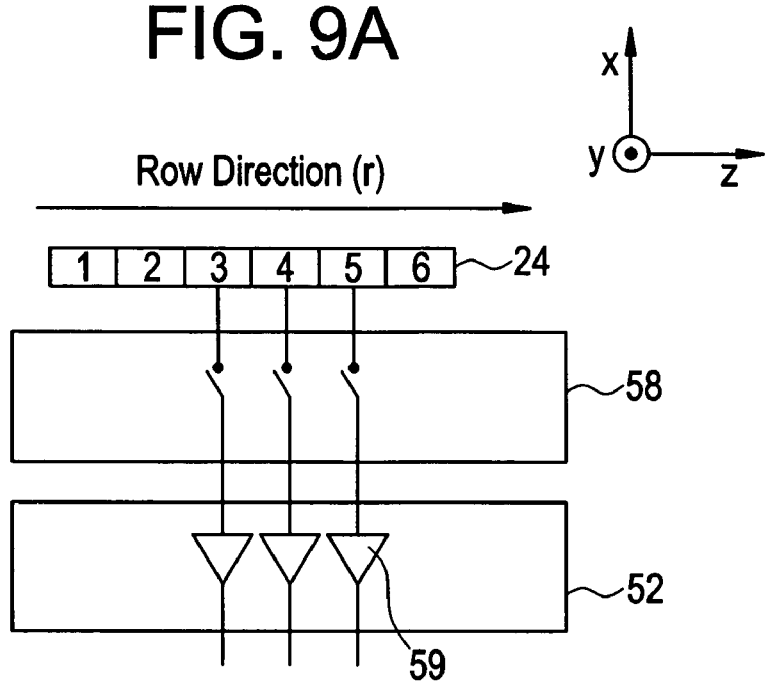
FIG. 9a is a block diagram and FIG. 9b is an explanatory diagram both showing the third detector selecting means of the embodiment (part 2).

FIG. 9 is a diagram showing the configuration of third detector selecting means 58 in which the number of rows is reduced and all the X-ray detectors 24 in the channel direction are used. FIG. 9(A) illustrates the X-ray detector 24, third detector selecting means 58 and receiving unit 52 as viewed in the row direction. Here, a channel-direction position i is an arbitrary channel number, and there is no difference in the present configuration due to the channel number. When each switch of the third detector selecting means 58 is turned on, the third detector selecting means 58 sets one row as the input of each receiver 59 of the receiving unit 52. In the example shown in FIG. 9(A), the X-ray detector 24 having channel numbers 3, 4 and 5 corresponds to the inputs of the respective receivers 59 of the receiving unit 52.

Figure 9B:
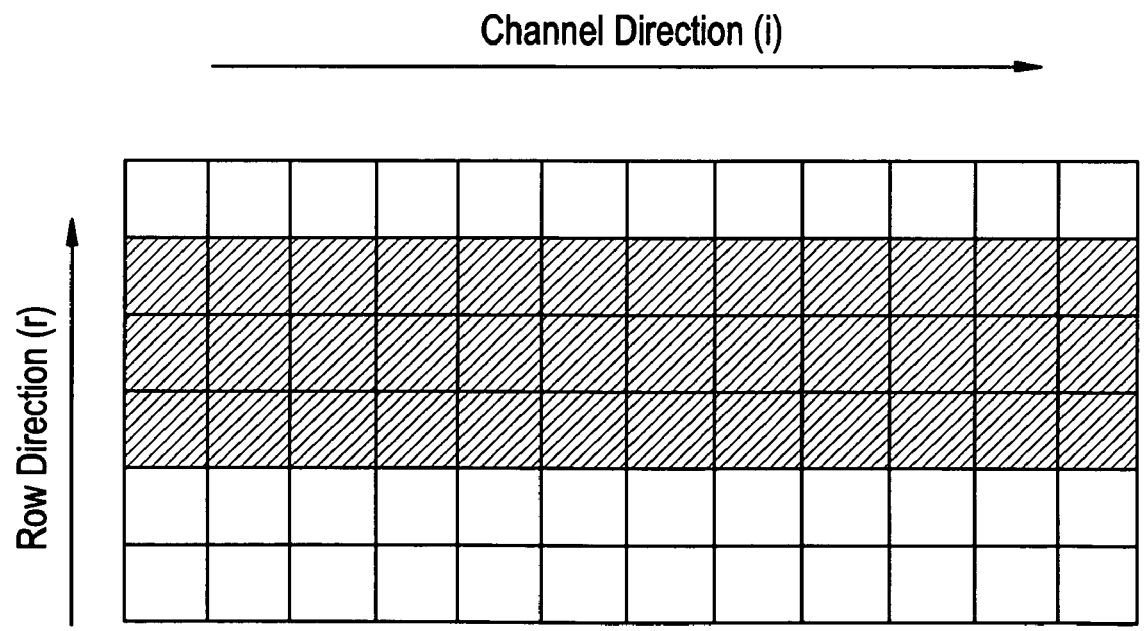

FIG. 9(B) is a diagram showing a two-dimensional arrangement in the channel and row directions, of the X-ray detectors 24 selected by the third detector selecting means 58. The X-ray detectors 24 in a diagonally shaded area of FIG. 9(B) perform reception and carry out acquisition of projection information. The third detector selecting means 58 may also share the use of these plural connections.

The operation of the X-ray CT apparatus according to the present embodiment will next be explained using FIG. 10. FIG. 10 is a flowchart showing the operation of the X-ray CT apparatus. An operator first places a subject to be examined in the neighborhood of the center of the bore 29 (Step S901).

Thereafter, the operator selects the X-ray detectors 24 (Step S902). Here, the operator operates the switching means 55 via the operating device 70 to select the first detector selecting means 56, second detector selecting means 57 or third detector selecting means 58 of the data acquisition section 26 according to imaging purposes.

When the first detector selecting means 56 is selected, the two X-ray detectors 24 lying in the channel direction are combined together to serve as a composite detector 25. The X-ray detectors 24 in the channel direction, which is equivalent to twice the number of receivers 59 that exist in the receiving unit 52, are used for imaging. The first detector selecting means 56 is capable of simultaneously collecting data extending over a wide imaging range in the channel direction by the receivers 59 small in number. Since the position of each composite detector 25 is moved by half of the repeated pitch thereof simultaneously with above as viewed in the row direction indicating the depth, the degradation of resolution can be rendered slight.

Figure 11:
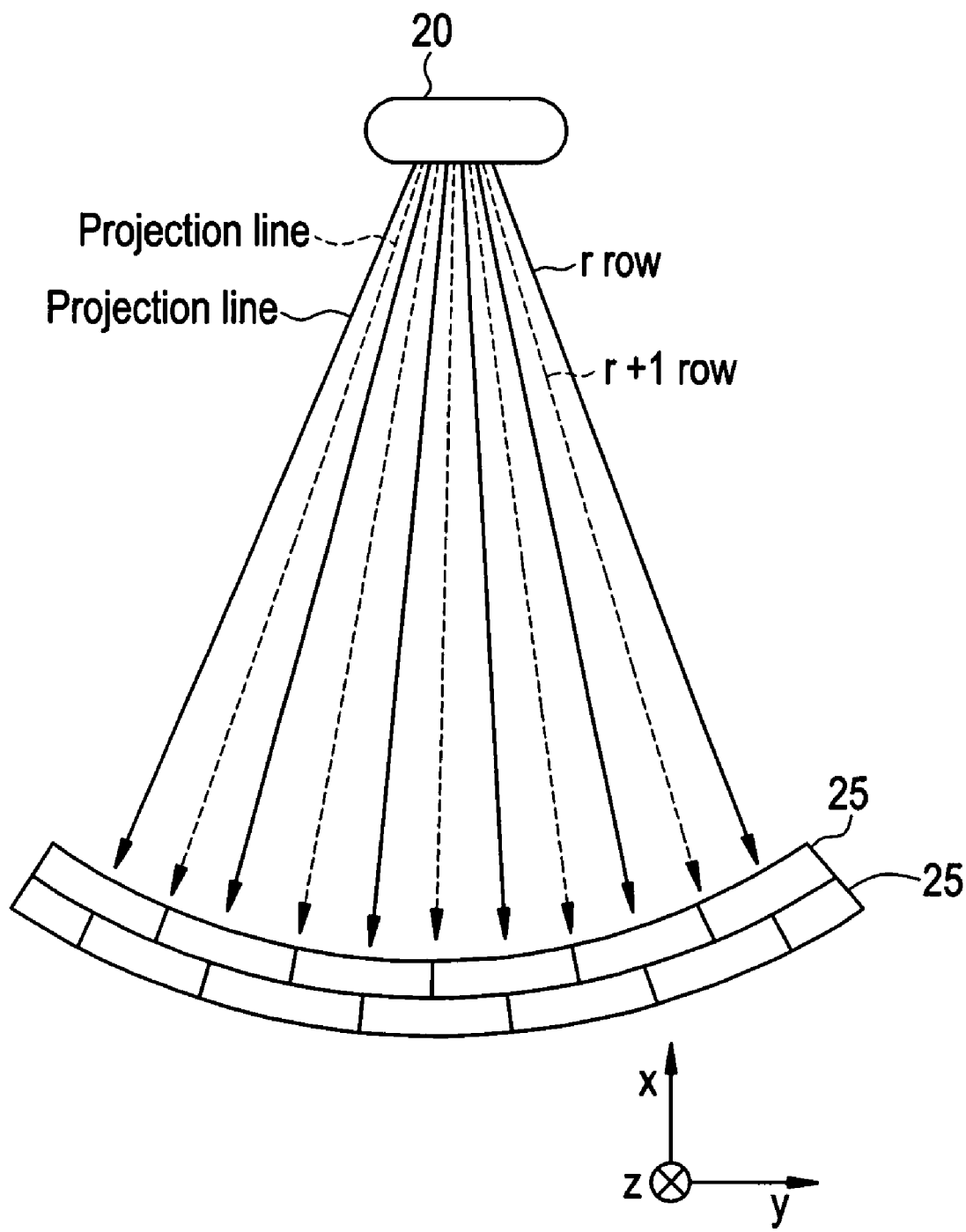
FIG. 11 is an explanatory diagram illustrating a reduction in resolution degradation by the first detector selecting means.

FIG. 11 illustrates projection lines where when imaging is done using the first detector selecting means 56, X rays radiated from the X-ray tube 20 are detected by the corresponding composite detectors 25. Incidentally, the array of composite detectors 25 in r+1 and r rows is shown in the figure in plane-developed form for reference.

Since the position of each of the composite detectors 25 in the r and r+1 rows is shifted by half of the repeated pitch in the channel direction as shown in FIG. 4, each of the composite detectors 25 results in one in which the position of each of the projection lines in the r and r+1 rows is shifted by a half pitch in FIG. 11. This brings about the effect of enhancing resolution of projection information in the channel direction. Hence the resolution degradation of an axial sectional image can be rendered slight.

When the second detector selecting means 57 is selected, two X-ray detectors 24 extending in a row direction are combined together to serve as a composite detector 27. The X-ray detectors 24 in the row direction, which is equivalent to twice the number of amplifiers that exist in the corresponding receiving unit 52, are used for imaging. Data extending over a wide imaging range in the row direction can simultaneously be collected by the receivers 59 small in number. Since the position of each composite detector 27 is moved by half of the repeated pitch thereof simultaneously with above as viewed in the channel direction, the degradation of resolution can be rendered slight due to the reason similar to that shown in FIG. 11.

When the third detector selecting means 58 is selected, the X-ray detector 24 and each receiver 59 of the receiving unit 52 is placed in a one-to-one correspondence. Although the imaging range becomes narrow, the detecting plane of X rays becomes small as compared with the composite detector 25 or 27 and hence imaging in high resolution is carried out.

Referring back to FIG. 10, the operator thereafter performs a scan (Step S903). Incidentally, the above-described first detector selecting means 56, second detector selecting means 57 and third detector selecting means 58 acquire operator-aimed images in combination with a helical scan, a conventional scan, a cine scan, etc.

When, for example, the helical scan is done, the first detector selecting means 56 is selected to perform imaging equivalent to the double number of rows as viewed in the row direction corresponding to the thickness direction while the degradation of resolution in the channel direction is being suppressed to a minor degree. On the other hand, the third detector selecting means 58 is selected, so that an image high in resolution as viewed in the channel direction is acquired although the number of rows is reduced.

Further, when the conventional scan is performed, the first detector selecting means 56 is selected to carry out imaging corresponding to the double number of rows as viewed in the row direction corresponding to the thickness direction while the degradation of resolution in the channel direction is being suppressed to a minor degree. Alternatively, the second detector selecting means 57 is selected to acquire an image high in resolution as viewed in the row direction while the degradation of resolution in the channel direction is being suppressed to a minor degree.

Thereafter, the operator displays the acquired image (Step S904) and finishes the present processing.

In the present embodiment as described above, such an array that the X-ray detectors 24 in the channel or row direction are operated with the two as one pair is made by the switching unit 51. This array moved by one X-ray detector 24 in the channel or row direction is alternately repeated in the row or channel direction. Therefore, even when the number of the receivers 59 is small, the data extending over the wide imaging range can simultaneously be collected while the degradation of resolution is being suppressed to the minor degree. By extension, imaging more coincident with the operator-aimed image can be done by making the switching use of imaging in high resolution.

Figure 12:
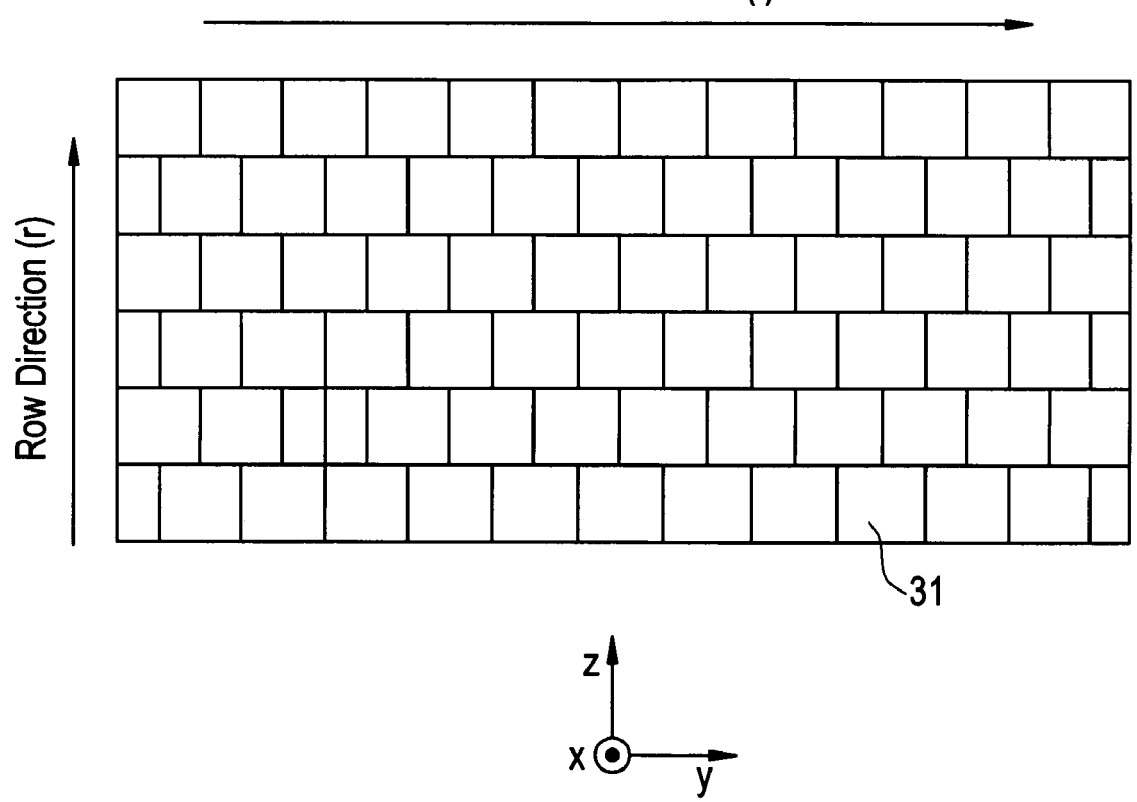
FIG. 12 is a layout diagram showing an example of another array of X-ray detectors arranged two-dimensionally.

Although the X-ray detectors 24 are two-dimensionally arranged in matrix form in the channel and row directions as shown in FIG. 2 in the present embodiment, X-ray detectors 24 each shifted by a half pitch in the channel or row direction can also repeatedly be disposed on an alternate basis as viewed in the row or channel direction. FIG. 12 shows an example illustrative of X-ray detectors 31 each shifted by a half pitch in a channel direction, whose movement arrangements are repeatedly placed alternately in a row direction. By doing so, the X-ray detectors 31 can further enhance resolution in the channel direction where the third detector selecting means 58 referred to above is selected. On the other hand, when the above first detector selecting means 56 is selected, the effect of suppressing degradation of the resolution in the channel direction becomes low as compared with the case in which the X-ray detectors are arranged in matrix form.

The charging of ends in the channel direction with half-pitch-sized X-ray detectors is repeatedly effected on X-ray detectors provided alternately in the row direction to thereby make it easy to fabricate the X-ray detectors 31 shown in FIG. 12 as perfect rectangles.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT apparatus comprising:
   an X-ray tube which applies a cone X-ray beam spread in a thickness direction thereof;
   an X-ray detector which is two-dimensionally arranged in a plane approximately orthogonal to the direction of application of the X-ray beam and which detects the X-ray beam and converts the same to an electric signal; and
   a data acquisition section having receivers each amplifying the electric signal,
   wherein the data acquisition section has a switching unit which turns on and off wirings for electrically connecting the X-ray detector and the receivers and selects the X-ray detector for performing said detection, and wherein the switching unit has composite detector selecting means placed within a plane of the two-dimensionally arranged X-ray detector and in which an electrical connection for allowing the two X-ray detectors adjacent in a coordinate-axis direction indicative of an X-ray detector position in the thickness direction or in a channel direction orthogonal to the thickness direction to operate as one composite detector is repeatedly performed in the coordinate-axis direction, and an electrical connection in which a position of said repetition of electrical connection is shifted in the coordinate-axis direction by one X-ray detector is performed between the X-ray detectors adjacent in an orthogonal-axis direction normal to the coordinate-axis direction.

2. The X-ray CT apparatus according to claim 1, wherein the composite detector selecting means has first detector selecting means in which the coordinate-axis direction is defined as the channel direction.

3. The X-ray CT apparatus according to claim 1, wherein the composite detector selecting means has second detector selecting means in which the coordinate-axis direction is defined as a row direction corresponding to the thickness direction of the X-ray beam.

4. The X-ray CT apparatus according to claim 1, wherein the switching unit has third detector selecting means which electrically connects one of the receivers with one of the X-ray detectors.

5. The X-ray CT apparatus according to claim 2, wherein the data acquisition section includes switching means which allows the first through third detector selecting means to operate by switching.

6. The X-ray CT apparatus according to claim 5, wherein the switching means performs switching to the third detector selecting means when a conventional scan or a cine scan is done.

7. The X-ray CT apparatus according to claim 6, wherein the switching means performs switching to the first or second detector selecting means when simultaneous collection of data, which is performed by the conventional scan or the cine scan, is carried out in a wider imaging range.

8. The X-ray CT apparatus according to claim 5, wherein the switching means performs switching to the third detector selecting means when a helical scan is done.

9. The X-ray CT apparatus according to claim 8, wherein the switching means performs switching to the first or second detector selecting means when simultaneous collection of data, which is performed by the helical scan, is carried out in a wider imaging range.

10. The X-ray CT apparatus according to claim 1, wherein the X-ray detector includes scintillators.

11. The X-ray CT apparatus according to claim 1, wherein the data acquisition section is accommodated in a rotational section including the X-ray tube and the X-ray detector.

12. The X-ray CT apparatus according to claim 1, wherein the switching unit includes FETs each of which performs said turning on/off.

13. The X-ray CT apparatus according to claim 1, wherein the data acquisition section includes the receivers smaller than the X-ray detectors in number.

14. The X-ray CT apparatus according to claim 4, wherein the third detector selecting means reduces the number of X-ray detectors selected in either the coordinate-axis direction or the orthogonal-axis direction.

15. The X-ray CT apparatus according to claim 1, wherein the X-ray detectors are configured in such a manner that the positions of the respective X-ray detectors arranged in the coordinate-axis direction are taken as the same positions as viewed in the orthogonal-axis direction.

16. The X-ray CT apparatus according to claim 1, wherein the X-ray detectors are configured in such a manner that an array of the X-ray detectors disposed at equal intervals in the coordinate-axis direction and a movement array in which the array thereof is shifted by half of said each equal interval in the coordinate-axis direction, are carried out between the X-ray detectors adjacent in the orthogonal-axis direction.

17. The X-ray CT apparatus according to claim 16, wherein the X-ray detectors include X-ray detectors whose each length in the coordinate-axis direction is equal to half of the X-ray detector, which are disposed at ends in the coordinate-axis direction, of the movement array.

18. The X-ray CT apparatus according to claim 1, wherein the X-ray detectors are configured in such a manner that an array of the X-ray detectors disposed at equal intervals in the orthogonal-axis direction and a movement array in which the array thereof is shifted by half of said each equal interval in the orthogonal-axis direction, are carried out between the X-ray detectors adjacent in the coordinate-axis direction.

19. The X-ray CT apparatus according to claim 18, wherein the X-ray detectors include X-ray detectors whose each length in the orthogonal-axis direction is equal to half of the X-ray detector, which are disposed at ends in the orthogonal-axis direction, of the movement array.

* * * * *